United States Patent
Finley et al.

(10) Patent No.: US 11,961,598 B1
(45) Date of Patent: Apr. 16, 2024

(54) MACHINE LEARNING SYSTEMS FOR ERROR DETECTION IN DATA PROCESSING SYSTEMS AND RELATED METHODS

(71) Applicant: Express Scripts Strategic Development, Inc., St. Louis, MO (US)

(72) Inventors: Morgan J. Finley, St. Louis Park, MN (US); Garret L. Anderson, Arden Hills, MN (US); Camille Patel, New York, NY (US); Michael Nassar, Chicago, IL (US); Siju Vattakunnumpurath Eugin, Parsippany, NJ (US); Daniel Owens, Pompton Plains, NJ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 834 days.

(21) Appl. No.: 16/913,797

(22) Filed: Jun. 26, 2020

(51) Int. Cl.
  *G16H 20/10* (2018.01)
  *G06F 16/28* (2019.01)
  *G06N 20/00* (2019.01)
  *G16H 40/20* (2018.01)

(52) U.S. Cl.
  CPC .......... *G16H 20/10* (2018.01); *G06F 16/283* (2019.01); *G06N 20/00* (2019.01); *G16H 40/20* (2018.01)

(58) Field of Classification Search
  CPC ....... G16H 20/00–90; G16H 40/00–67; G06N 20/00–20
  See application file for complete search history.

(56) References Cited

U.S. PATENT DOCUMENTS

| | | | |
|---|---|---|---|
| 10,204,312 B2 | 2/2019 | Singh | |
| 10,291,838 B2 | 5/2019 | Zhou | |
| 2017/0262552 A1* | 9/2017 | Noma | G06F 16/90335 |
| 2018/0218369 A1* | 8/2018 | Xiao | G06Q 20/20 |
| 2019/0371472 A1 | 12/2019 | Blanchard | |
| 2020/0005947 A1 | 1/2020 | Blanchard | |
| 2020/0034842 A1* | 1/2020 | Ponniah | G06Q 40/03 |
| 2020/0051172 A1 | 2/2020 | Agnew | |
| 2020/0152332 A1 | 5/2020 | Yang | |
| 2020/0279200 A1 | 9/2020 | Makhija | |
| 2020/0286016 A1 | 9/2020 | Singh | |
| 2020/0320548 A1 | 10/2020 | Fusillo | |

* cited by examiner

*Primary Examiner* — Mohammad A. Nilforoush
(74) *Attorney, Agent, or Firm* — Stinson LLP

(57) ABSTRACT

A method for predicting errors in prescription claim data is performed by a claim analysis device. The method includes extracting historical claim features from successfully processed historical claims received from the data warehouse system. The method includes extracting pending claim features from a pending claim. The method includes applying a binarization process on the extracted historical claim features to obtain a binarized training feature set. The method includes applying the binarization process on the extracted pending claim features to obtain a binarized pending feature set. The method includes calculating an aggregate distance between the binarized pending feature set and the binarized training feature set. The method includes identifying the historical claim associated with the least aggregate distance as a predictive historical claim. The method includes transmitting an alert upon determining that a billing attribute of the predictive historical claim fails to match a corresponding billing attribute of the pending claim.

20 Claims, 9 Drawing Sheets

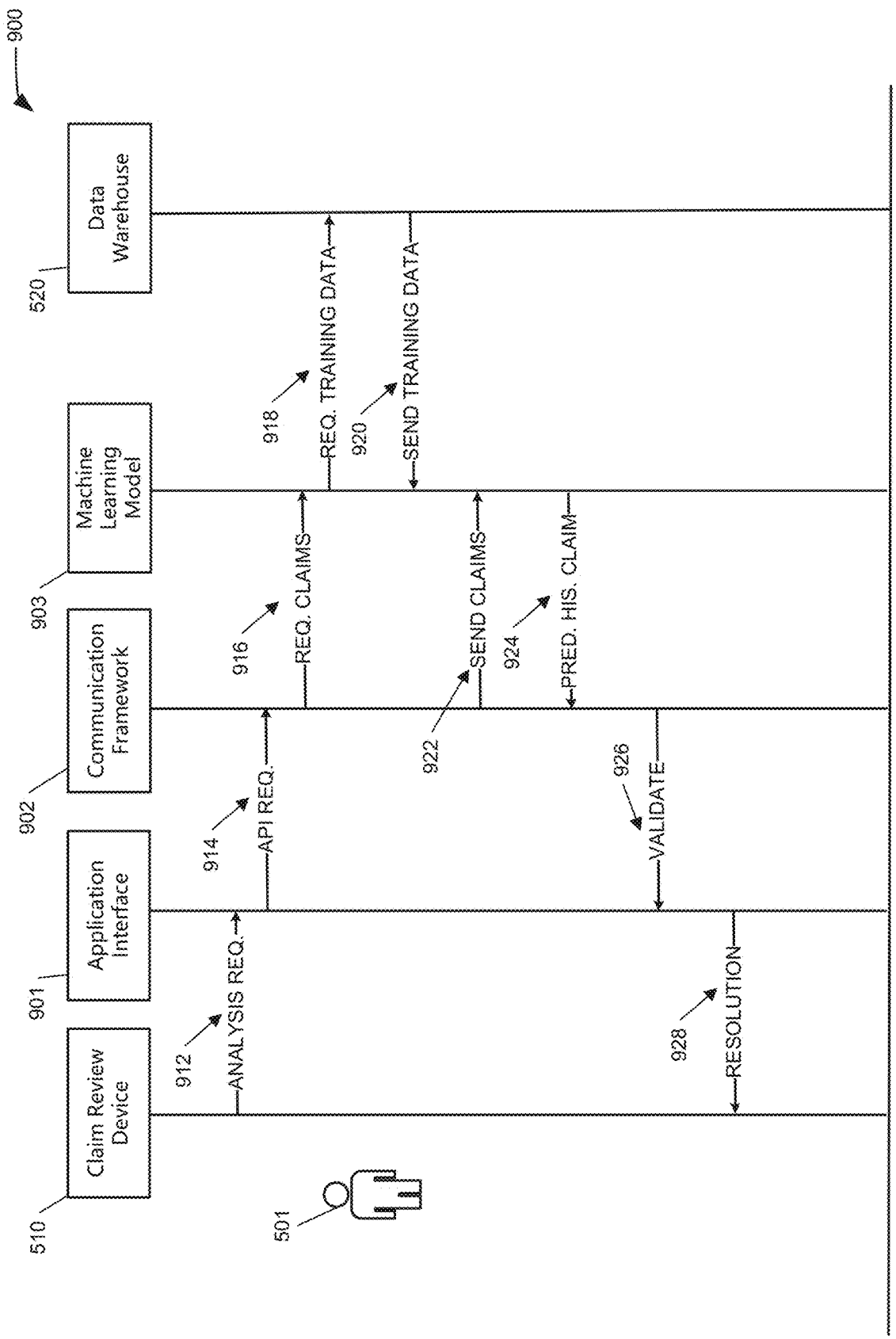

MACHINE LEARNING SYSTEMS FOR ERROR DETECTION IN DATA PROCESSING SYSTEMS AND RELATED METHODS

FIELD OF INVENTION

The field relates to machine learning systems for reducing error rates in complex data systems and, more specifically, to machine learning systems for identifying and correcting potential errors in data sets.

BACKGROUND OF THE DISCLOSURE

In many known data processing systems, there is often a significant risk associated with erroneous data. Erroneous data or inaccurate data can impair or prevent the processing of data records, often with significant adverse consequences for systems and parties related to the records.

When data is provided with incorrect terms, related records may not be able to be processed accurately or at all. The consequences of failed, impaired, or delayed processing can be significant. For example, data processing systems may be used to process information necessary for crucial services such as medical treatment or medical prescriptions. When data processing is impaired, delayed, or blocked by inaccurate or erroneous data in such important systems, end users may be affected by being delayed or denied in receipt of prescriptions or medical care. In other examples, inaccurate or erroneous data may cause parties to fail to receive necessary payment for services.

Automated detection of errors or inaccuracies in data sets may be difficult to identify using known systems. In many cases, the relationship between the individual records and certain characteristics are not static over time, and therefore not predictable using a static set of rules or a model because trends in underlying data sets may vary over time. The reason that static rules cannot identify errors is because conditions change frequently, altering the relationships between elements of records and related characteristics. Nevertheless, it is crucial that data processing systems determine some of these characteristics as early as possible in the information cycle of processing the data records. In the context of medical or prescription records, the need to identify inaccuracies in crucial terms such as billing terms is urgent.

To address problems related to erroneous or inaccurate data, known systems conduct manual review of individual data records to identify potential inaccurate or erroneous data. Such review is time consuming and often entails individual verification of records. However, in addition to being time intensive, such review can also introduce secondary errors into data records. For example, individual reviewers (or parties with whom reviewers verify records) may inadvertently flag accurate records as inaccurate and make unnecessary and improper edits, flag inaccurate records but make improper edits to fix the inaccuracies, or fail to identify inaccuracies altogether. As a result, known systems have the undesirable results of being inefficient and ineffective.

As such, machine learning systems for reducing error rates in complex data systems such as medical or prescription billing systems, prior to order processing, are desirable.

BRIEF SUMMARY OF THE INVENTION

In one aspect, a machine learning system for predicting errors in prescription claim data is provided. The machine learning system includes a data warehouse system, a claim processing system, and a claim analysis device. The data warehouse system includes a data warehouse processor and a data warehouse memory. The data warehouse system includes historical claims. The historical claims include historical claim features and a historical claim status. The claim processing system includes a system processor and a system memory. The claim processing system includes pending claims, and the pending claims include pending claim features. The claim analysis device is in communication with the data warehouse system and the claim processing system. The claim analysis device includes a processor and a memory. The processor is configured to extract historical claim features from historical claims received from the data warehouse system. The historical claims have a corresponding historical claim status indicating that the claims have been successfully processed. The processor is also configured to extract pending claim features from a pending claim received from the claim processing system. The processor is further configured to apply a binarization process on the extracted historical claim features to obtain a binarized training feature set for the historical claims. The processor is further configured to apply the binarization process on the extracted pending claim features to obtain a binarized pending feature set for the pending claim. The processor is also configured to calculate an aggregate distance between the binarized pending feature set and the binarized training feature set for the historical claims. The processor is additionally configured to identify the historical claim associated with the least aggregate distance as a predictive historical claim. The processor is also configured to transmit an alert upon determining that a billing attribute of the predictive historical claim fails to match a corresponding billing attribute of the pending claim.

In another aspect, a method for predicting errors in prescription claim data is provided. The method is performed by a claim analysis device in communication with a data warehouse system and a claim processing system. The data warehouse system includes historical claims including historical claim features and a historical claim status. The claim processing system includes pending claims including pending claim features. The claim analysis device includes a processor and a memory. The method includes extracting historical claim features from historical claims received from the data warehouse system. The historical claims have a corresponding historical claim status indicating that the claims have been successfully processed. The method also includes extracting pending claim features from a pending claim received from the claim processing system. The method further includes applying a binarization process on the extracted historical claim features to obtain a binarized training feature set for the historical claims. The method also includes applying the binarization process on the extracted pending claim features to obtain a binarized pending feature set for the pending claim. The method additionally includes calculating an aggregate distance between the binarized pending feature set and the binarized training feature set for the historical claims. The method also includes identifying the historical claim associated with the least aggregate distance as a predictive historical claim. The method includes transmitting an alert upon determining that a billing attribute of the predictive historical claim fails to match a corresponding billing attribute of the pending claim.

In yet another aspect, a claim analysis device is provided for predicting errors in prescription claim data. The claim analysis device is in communication with a data warehouse system and a claim processing system. The data warehouse system includes historical claims, and the historical claims include historical claim features and a historical claim status. The claim processing system includes pending claims. The pending claims include pending claim features. The claim analysis device includes a processor and a memory. The processor is configured to extract historical claim features from historical claims received from the data warehouse system. The historical claims have a corresponding historical claim status indicating that the claims have been successfully processed. The processor is configured to extract pending claim features from a pending claim received from the claim processing system. The processor is further configured to apply a binarization process on the extracted historical claim features to obtain a binarized training feature set for each historical claim. The processor is also configured to apply the binarization process on the extracted pending claim features to obtain a binarized pending feature set for the pending claim. The processor is further configured to calculate an aggregate distance between the binarized pending feature set and the binarized training feature set for each historical claim. The processor is also configured to identify the historical claim associated with the least aggregate distance as a predictive historical claim. The processor is further configured to transmit an alert upon determining that a billing attribute of the predictive historical claim fails to match a corresponding billing attribute of the pending claim.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 9 is a flow diagram representing an exemplary process performed by the machine learning system of FIG. 5 to predict errors in data processing systems.

In the drawings, reference numbers may be reused to identify similar and/or identical elements.

DETAILED DESCRIPTION

Figure 1:
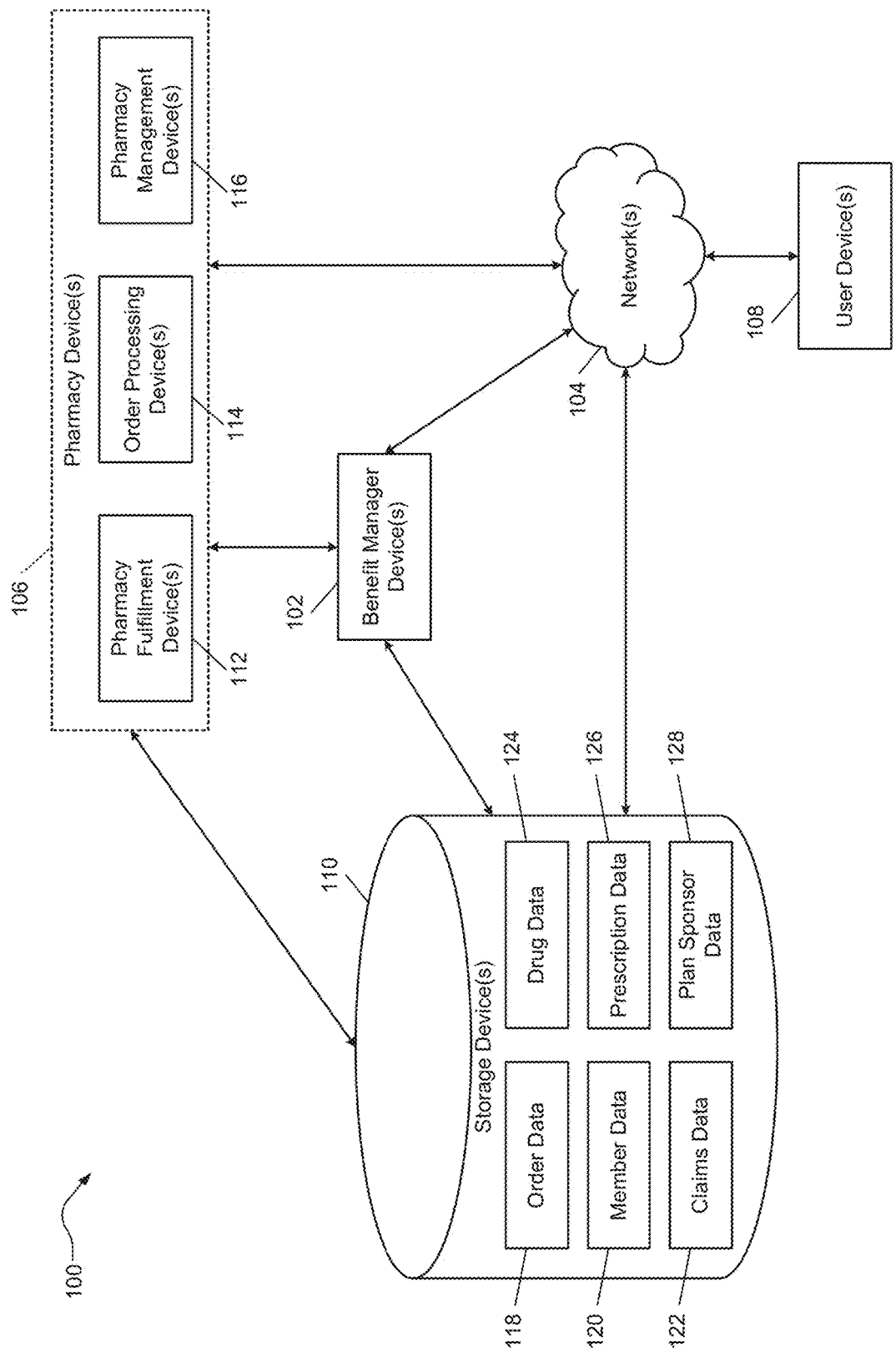
FIG. 1 is a functional block diagram of an example system including a high-volume pharmacy.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein, the term "feature extraction" or "extraction" refers to the process of selecting a subset of relevant features (e.g., variables or predictors) from a data set that are used in the described machine learning system to predict erroneous or inaccurate data and define data models. Feature extraction or extraction may alternatively be described as variable selection, attribute selection, or variable subset selection. "Features" as used herein, refer to characteristics, components, or elements of data sets. In particular, features may refer to particular characteristics or components of claims. The feature selection process of the machine learning system described herein allows the machine learning system to efficiently predict errors in prescription claim data.

As used herein, the term "nearest neighbor algorithm" (also known as "k-nearest neighbor algorithm") refers to a non-parametric method used for classification and regression. In both cases, the input includes the k closest training examples in the feature space. Like the random forest algorithm, nearest neighbor algorithm may be used for classification or regression and may determine a class membership or object property value, respectively. Generally, the nearest neighbor algorithm involves assigning greater weight to the contributions of the nearer neighbors, so that the nearer (or proximate) neighbors contribute more to the average than the more distant ones. In one example, each neighbor is assigned a weight of 1/d, where d is the distance to the neighbor, and where the weight of the neighbor is thus inverse to the distance from the neighbor.

As used herein, the term "binarization" refers to the process of converting data features into a binary format to allow for efficient computation and classification of such data features. By converting data features that are otherwise represented as, for example, integers or strings, into binary vectors or binary numbers, such data features can be efficiently processed and compared. Further, the use of binarization significantly reduces memory utilization in complex analysis and comparison of features.

As used herein, the term "Hamming distance" refers to a metric in information theory used to compare the difference between binary data strings such as data features that have been binarized. The Hamming distance between two words a and b can also be seen as the Hamming weight of a-b for an appropriate choice of the—operator, much as the difference between two integers can be seen as a distance from zero on the number line. In some examples, a minimum Hamming distance is used to define some essential notions in coding theory, such as error detecting and error correcting codes. In particular, a code C is said to be k error detecting if, and only if, the minimum Hamming distance between any two of its codewords is at least k+1.

The machine learning systems and methods described herein are configured to address known technological problems confronting computing systems and networks that process data sets, specifically the problems that arise in data processing systems with risks of erroneous or inaccurate data. In particular, in the context of prescription and medical billing, erroneous or inaccurate data can cause significant problems in data processing. When data processing is impaired, delayed, or blocked by inaccurate or erroneous data in such important systems, end users may be affected by being delayed or denied in receipt of prescriptions or medical care. In other examples, inaccurate or erroneous data may cause parties to fail to receive payment for services. Notably, when a particular claim is tied to the wrong benefit category (e.g., pharmacy rather than medical or vice versa), significant operational errors or complexities may arise. For example, when claims are filed with the wrong benefit category, an organization processing a claim (e.g., a pharmacy) may be forced to write off the cost of the pharmacy. In other examples, a patient with long term prescriptions may experience delays in prescription delivery as a result of improper benefit data.

The machine learning systems and methods described are configured to address these known problems particularly as they relate to determining whether a medical claim is associated with the correct benefit. Benefits are typically defined as either medical or pharmacy. By utilizing historic data regarding successfully processed claims, the machine learning systems described utilize the corpus of that data to identify salient features for extraction. The extracted features of the historic data are then applied to a machine learning algorithm to identify a historic claim that most corresponds to a particular pending claim under analysis. The machine learning system performs binarization on the extracted features of the pending claim and the historic claims to identify the most similar historic claim as a predicted historic claim. By processing the binarized feature sets for each of the historic claims and the pending claim, the machine learning system identifies the historic claim that is the nearest neighbor to the pending claim, and therefore the historic claim that is best used to predict the billing attribute of the pending claim. The machine learning system also monitors for discrepancies in the billing attribute as between the pending claim and the predictive historic claim. If a discrepancy exists, the machine learning system may transmit an alert to identify the discrepancy, automatically correct the discrepancy, or recommend a correction of the discrepancy. If no discrepancy exists, the machine learning system validates the billing attribute of the pending claim. As such, the machine learning systems and methods described overcome known deficiencies in previous technological approaches. Previous known methods involve either the application of static data models which tend to become more inaccurate over time, or utilize manual review which is both inefficient and error prone.

By contrast, the machine learning systems and methods provided allow the claim analysis device to adjust to changes in data records based on external or systematic changes. By utilizing historic claim data related to recent successfully processed claims, the machine learning system applies the most relevant and high quality training data for prediction of errors, correction of errors, or validation. In an example embodiment, the machine learning system has achieved an error prediction accuracy level that matches or exceeds 99.8%.

Therefore, to overcome known problems of determining whether a claim for prescription or medical benefits requires a particular billing attribute, a machine learning system is provided. The machine learning system is capable of performing predictive modeling based on extracted features of training data sets and applying the model to pending claims. Once the machine learning system is trained, the predictive models it generates accurately predict which claim benefit should apply to a given pending claim. In the example embodiment, the machine learning system includes at least a claim processing system and a data warehouse system. The machine learning system also includes a claim analysis device that is in communication with the data warehouse system and the claim processing system.

The machine learning system is used to predict errors and inaccuracies in prescription claim data. The data warehouse system includes a data warehouse processor and a data warehouse memory. The data warehouse system includes historical claims for prescriptions. As described herein, claim data (including historical claims and pending claims) have "features" or "claim features" representing elements or components of the claims. Relevant example features are described in detail below. The historical claims also include a historical claim status indicating whether each historical claim was successfully processed. Notably, historical claim features also include relevant processing information including the date and time of processing. The machine learning system also includes a claim processing system. The claim processing system includes a system processor and a system memory. The claim processing system includes pending claims which each include a set of pending claim features. The machine learning system also includes a claim analysis device that is in communication with the data warehouse and the claim processing system. In some examples, all systems and devices of the machine learning system are in communication with one another.

The claim analysis device receives a subset of historical claims from the data warehouse for use as training data. In the example embodiment, each historical claim of the subset of historical claims was successfully processed for payment. In some examples, the subset of historical claims are the n most recent historical claims that were successfully processed for payment. N may be any suitable value for a system and may be determined based on, for example, the daily or weekly volume of historical claims in the data warehouse. In other examples, the subset of historical claims are all historical claims that were successfully processed for payment within the past x hours or days. In further examples, the subset of historical claims includes a representative sample reflecting each billing attribute option. In situations where billing attributes may be "medical" or "pharmacy", the subset of historical claims may be the past n/2 most recent historical claims that were successfully processed for payment for each of medical billing and pharmacy billing. In some examples, the claim analysis device requests the training data. In such examples, the claim analysis device transmits a request to the data warehouse system for the subset of historical claims and receives the subset of historical claims from the data warehouse system.

The claim analysis device also extracts a subset of historical claim features from each of the subset of historical claims. As described herein, the "features" that are extracted are features that are included within historical claims and pending claims. As such, the features define the corpus of training data (i.e., the subset of historical claims) and the pending claims in part or in whole. The features identified for extraction reflect features that may be salient in predicting billing attributes. In one example, the claim analysis device identifies a list of features for feature extraction based on a feature analysis profile. The feature analysis profile may be a record defined in the claim analysis device defining the features. In many examples, the list of features for feature extraction may be updated or otherwise changed over time. The claim analysis device extracts the subset of historical claim features matching the list of features and the subset of pending claim features matching the list of features. In some examples, the "features" are defined to include at least one of: a) a National Council for Prescription Drug Program ("NCPDP") Processor ID Number or "Benefit Identification Number" (known otherwise as "BIN"); b) a processor control number ("PCN"); c) a member identification number ("Member ID"); and d) a therapy type (i.e., the name of the drug or therapy prescribed).

The claim analysis device also extracts a subset of historical claim features from each of the subset of historical claims. The claim analysis device also extracts a subset of pending claim features from a pending claim received from the claim processing system. In the example embodiment, the claim analysis device processes selected pending claims on an individual basis. Each pending claim may be selected in any suitable fashion including, for example, by selecting the most recent pending claim, the oldest pending claim, any pending claim at risk of falling past a relevant jurisdictional processing timeline, random selection, or flagging based on user or automated input. In some examples, the claim analysis device selects the most recent pending claim to, for example, prioritize throughput of new claims while in other examples the claim analysis device selects the oldest pending claim to, for example, avoid backlogs. In other examples, particular jurisdictions may set a maximum time that a claim may be pending. In such examples, the claim analysis device selects the claims that are closes to approaching such a maximum processing time to avoid the risk of a claim not meeting jurisdictional requirements. In other examples, the claim analysis device selects claims randomly to, for example, balance processing across groups. In further examples, the claim analysis device identifies flagged claims that may require further attention. Flagging may be performed automatically or by a user. In such embodiments, the claim analysis device is process a pending claim for predicting errors in billing attributes. In some embodiments, the claim analysis device processes multiple pending claims in parallel using the same methodology otherwise described. In some embodiments, the claim analysis device also initiates a request to the claim processing system which is prompted to provide the pending claim (or pending claims). In some examples, when the claim processing system provides multiple pending claims, the claim analysis device is configured to select an individual claim for analysis, as described above, or to select multiple claims for analysis in parallel.

The claim analysis device also applies a binarization process on the extracted subsets of historical claim features to obtain a binarized training feature set for each historical claim. As described, the claim analysis device reads in, or processes, each set of historical claim features for each historical claim before binarizing the features. Binarization is an important process because the task of calculating distances and choosing between nearest neighbors is a memory intensive activity for a processor. The activity of binarization during serves to speed up processing. In one embodiment, the claim analysis device provides data to (or within) a user-facing application integrating in to the workflow front-end. Binarization improves the speed (or efficiency) of preprocessing the machine learning models described herein. In some examples, preprocessing occurs on a daily basis (or other scheduled basis) without slowing the review, error detection, validation, and correction processes. In the example embodiment, the claim analysis device defines the binarization process as encoding each feature of a feature set in a corresponding binary format. Specifically, the claim analysis device defines a numeric representation of each feature of the feature set using suitable methods. For example, where a given feature includes a string, the numeric representation is determined based on the corresponding definitions as given by character definition protocols such as the American Standard Code for Information Interchange ("ASCII"), Unicode, or any other coding protocol or extension. The claim analysis device is similarly capable of binarizing any data type as needed using suitable methods for binarizing data including images, video, media, or audio. Similarly, the claim analysis device applies the binarization process on the extracted pending claim features to obtain a binarized pending feature set for the pending claim.

The claim analysis device processes the training data from the subset from the historical claims (and, more specifically, the binarized training feature set obtained after binarizing the extracted subsets of historical claim features) and compares training data to the processed claim data (and, more specifically, the binarized pending feature set obtained after binarizing the extracted pending claim features) to identify the historical claim that is the k-nearest neighbor to the pending claim under analysis. (In embodiments where several pending claims are simultaneously analyzed, the claim analysis device similarly processes each pending claim and compares each to each of the subset of historic claims to identify the k-nearest neighbor that is nearest to each pending claim.) In pattern recognition, the k-nearest neighbors algorithm (k-NN) is a method used for data analysis including classification and regression. Generally, the input includes the k closest training examples in a "feature space". Here, the training examples are the training data generated from the historical claims or, more specifically the subset of historical claims that are typically recent successfully processed and paid claims that are representative of multiple categories of billing attributes. In this case, the claim analysis device is configured to provide an output classifying one historical claim as a nearest neighbor (where k=1) and identifies that neighbor as a predictive historical claim. As such, the claim analysis device compares the billing attribute of the predictive historical claim to the billing attribute of the pending claim that is being analyzed.

To determine the nearest neighbor, the claim analysis device calculates an aggregate distance between the binarized pending feature set and the binarized training feature set for each historical claim. In the example embodiment, the claim analysis device calculates a distance between each feature of the binarized pending feature set and each corresponding feature of each binarized training feature set for each historical claim. The claim analysis device processes the distance determined for each feature of the binarized pending feature set and each corresponding feature of each binarized training feature for each historical claim and determines the aggregate distance between the binarized pending feature set and the binarized training feature set for each historical claim. In other words, the claim analysis device determines distances between the binarized pending feature set and each of the training feature set on a feature-by-feature basis and compounds the individual distances into an aggregate determination. In one example, the aggregation is a summation of each component distance. In another example, the aggregation is determined by weighting each component based on the relative significance of each feature, and summing the weighted components. In the example embodiment, the claim analysis device calculates the distance between each feature as a Hamming distance, and thereby calculates the aggregate distances based on a calculated Hamming distance between the binarized pending feature set and the binarized training feature set for each historical claim. A Hamming distance is a method to calculate a relative "distance" (or differentiation) between two binary values. Since binary numbers are based on a two-bit system, the difference between two bits of a binary number can be zero or one. However, when considering more complex features that have been binarized, the summation of distances between each bit can be used to differentiate the location of each candidate nearest neighbor with respect to the pending claim for a given feature. Similarly, the summation of the distances between each feature of the feature sets are used to differentiate the relative distance and location of the neighbors.

For clarity, illustrative examples are provided for binary distance calculations. As a first example, consider the distance between the values "100" and "200". These examples are provided for simplicity, but may stand in as example values for feature sets. In arithmetic calculation, the difference is "100". To determine a binarized distance, the values are first converted to binary where "100" results in a value of "01100100" and "200" results in a value of "11001000". The difference is determined by a comparison between each binary value of each binary string. First, each unit of each binary string is compared to the corresponding unit of the corresponding string which, in this case, is "1010110". Each element that is different is then added arithmetically, resulting in a value of "4". In a second example, the distance between the values "100" and "111" is compared. In arithmetic calculation, the difference is "11". The binary value of "100" is "01100100" and the binary value of "111" is "01101111". Thus, the comparison results in a determination of "0001011". The arithmetic computation of this difference results in a value of "3".

The claim analysis device is configured to identify the historical claim associated with the least (or lowest) aggregate distance as the nearest neighbor to the pending claim and, therefore, as a predictive historical claim. The predictive historical claim is necessarily a claim that is predicted to have a billing attribute that should be used by the pending claim. In some examples, the claim analysis may determine that more than one historical claim is associated with the least (or lowest) aggregate distance, and therefore more than one historical claim is a nearest neighbor having the same distance from the pending claim. In such cases, the claim analysis device may further analyze each of the candidate nearest neighbors. If the candidate nearest neighbors have matching billing attributes (or another characteristic that is validated by the claim analysis device), the claim analysis device may proceed to validate the pending claim based on the matching billing attribute value. If the candidate nearest neighbors do not have matching billing attributes, the claim analysis device may either flag the analysis as leading to an inconsistent prediction and provide an alert to a user device (such as a claim review device that is in communication with the claim analysis device and the machine learning system) and/or recommend one of the candidate nearest neighbors. The claim analysis device may make such a recommendation because one of the candidates is newer than the other or because the claim analysis device determines that one historical claim is a likely outlier and recommend another.

In operation, therefore, consider an example of a pending claim with a features that may be compared with the historical claims features. The claim analysis device determines that the pending claim feature includes feature values that are decomposed, processed, and/or binarized. Likewise, the feature values of the historical claims are decomposed, processed, and/or binarized. In this example, the feature values include at least one of: a) a National Council for Prescription Drug Program ("NCPDP") Processor ID Number or "Benefit Identification Number" (known otherwise as "BIN"); b) a processor control number ("PCN"); c) a member identification number ("Member ID"); and d) a therapy type (i.e., the name of the drug or therapy prescribed).

In one example, the pending claim includes these features that are binarized to result in a value of "01100100" while two historical claims are binarized to result in a value of "11001000" for a first historical claim and "01101111" for a second historical claim. The difference is determined by a comparison between each binary value of each binary string. The claim analysis device compares the binarized value of the pending claim features to the binarized values of the historical claim features. First, each unit of each binary string is compared to the corresponding unit of the corresponding string which, in this case. Each element that is different is then added arithmetically. Thus the claim analysis device determines that the pending claim has a distance of "4" with respect to the first historical claim and a distance of "3" with respect to the second historical claim. The claim analysis device identifies the historical claim associated with the least aggregate distance (the second historical claim here) as a predictive historical claim. In many examples, the claim analysis device performs these calculations using multiple historical claims and comparing multiple features.

Upon identifying a nearest neighbor as a predictive historical claim, the claim analysis device is configured to validate the pending claim (or pending claims, if analyzed in parallel) by comparing the billing attribute of the predictive historical claim (or the matching billing attributes, where more than one predictive historical claim is identified.) If the claim analysis device determines that the billing attributes match in both the pending claim and the predictive historical claim(s), the claim analysis device is configured to validate the match. In some examples, the claim analysis device transmits a confirmation message or alert message to a claim review device in communication with the machine learning system and the claim analysis device. In other examples, upon validation, the claim analysis device proceeds to the next pending claim for analysis. If the claim analysis device determines that the billing attributes do not match in both the pending claim and the predictive historical claim(s), in some examples the claim analysis device transmits an error or an alert message to a claim review device in communication with the machine learning system and the claim analysis device. In other examples, if the claim analysis device determines that the billing attributes do not match in both the pending claim and the predictive historical claim(s) the claim analysis device may alter the billing attribute of the pending claim to match the predictive historical claim(s) or alert a user to alter the billing attribute in such a manner by sending an alert message to, for example, a claim review device.

Generally, the systems and methods described herein are configured to perform at least the following steps: (a) extract a subset of historical claim features from each of a subset of historical claims received from the data warehouse system, wherein each of the subset of historical claims has a corresponding historical claim status indicating that the claim has been successfully processed; (b) extract a subset of pending claim features from a pending claim received from the claim processing system; (c) apply a binarization process on the extracted subsets of historical claim features to obtain a binarized training feature set for each of the subset of historical claims; (d) apply the binarization process on the extracted pending claim features to obtain a binarized pending feature set for the pending claim; (e) calculate an aggregate distance between the binarized pending feature set and the binarized training feature set for each of the subset of historical claims; (f) identify the historical claim associated with the least aggregate distance as a predictive historical claim; (g) transmit an alert upon determining that a billing attribute of the predictive historical claim fails to match a corresponding billing attribute of the pending claim; (h) calculate a distance between each feature of the binarized pending feature set and each corresponding feature of each binarized training feature set for each of the subset of historical claims; (i) process the distance determined for each feature of the binarized pending feature set and each corresponding feature of each binarized training feature for each of the subset of historical claims, to determine the aggregate distance between the binarized pending feature set and the binarized training feature set for each of the subset of historical claims; (j) calculate the aggregate distances based on a calculated Hamming distance between the binarized pending feature set and the binarized training feature set for each of the subset of historical claims; (k) define the binarization process as encoding each feature of a feature set in a corresponding binary format; (l) identify a list of features for feature extraction based on a feature analysis profile; (m) extract the subset of historical claim features matching the list of features; (n) extract the subset of pending claim features matching the list of features; (o) identify the list of features for feature extraction including at least one of a processor identification number, a processor control number, and a therapy type; (p) transmit a request to the data warehouse system for the subset of historical claims with corresponding historical claim statuses indicating that the claims have been successfully resolved; (q) receive the subset of historical claims from the data warehouse system; (r) receive the pending claim from the claim processing system; and (s) receive the subset of historical claims from the data warehouse system, wherein each of the subset of historical claims have corresponding historical claim statuses indicating that the claim has been successfully resolved.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
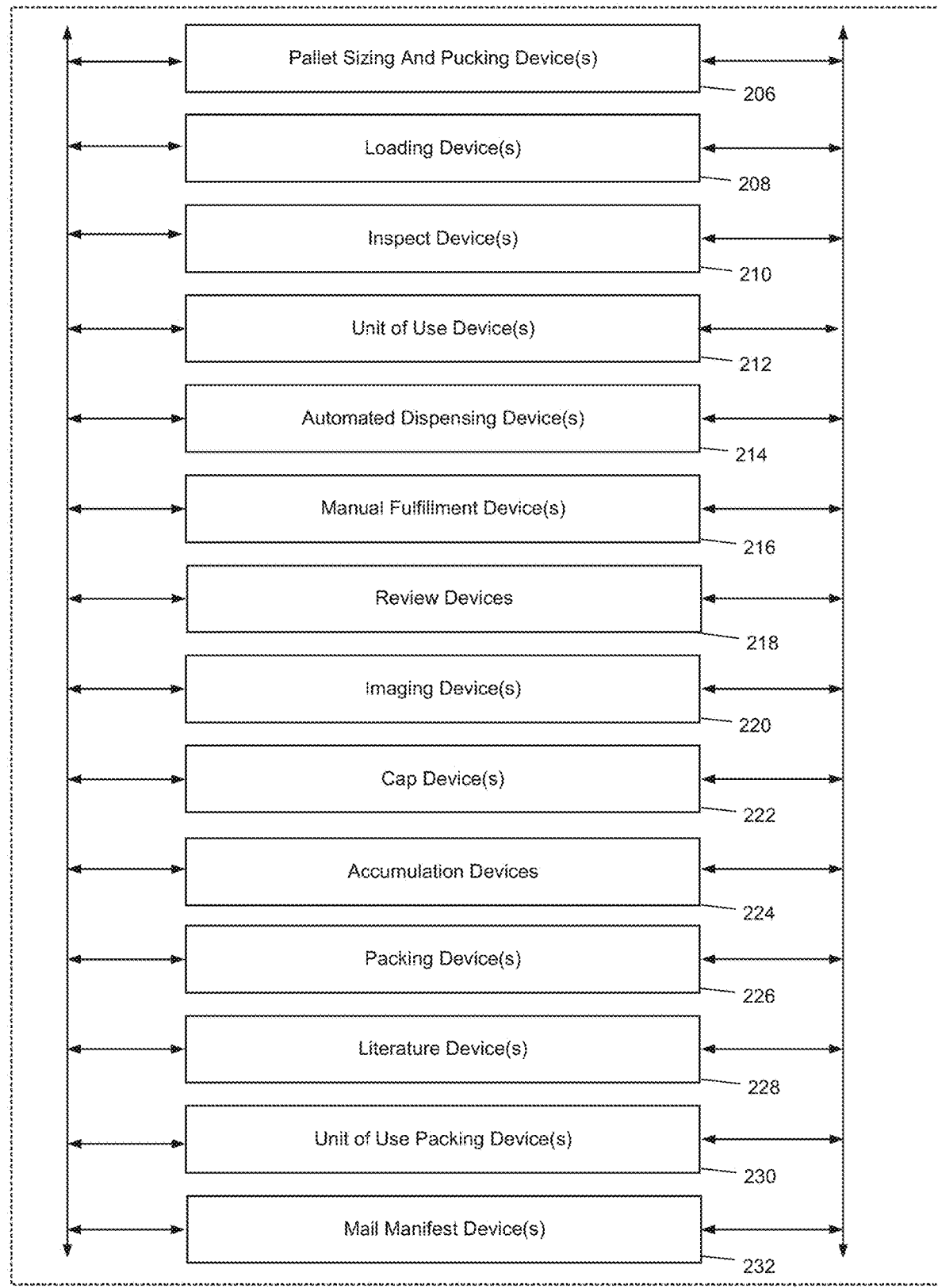
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
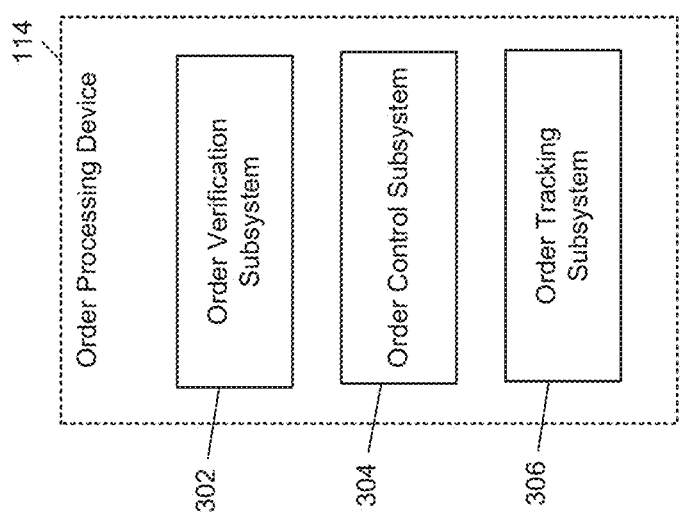
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Figure 4:
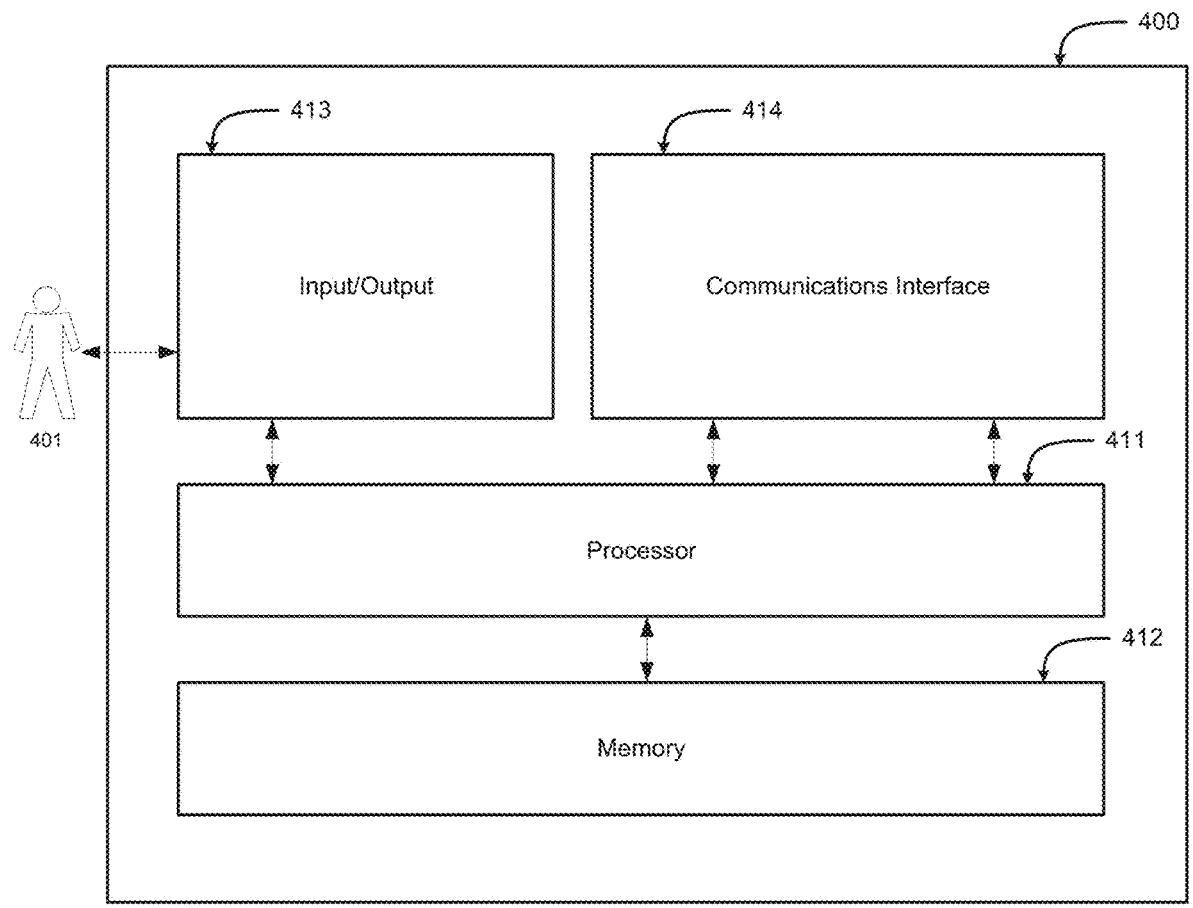
FIG. 4 is a functional block diagram of an example computing device that may be used in the machine learning system described.
Figure 5:
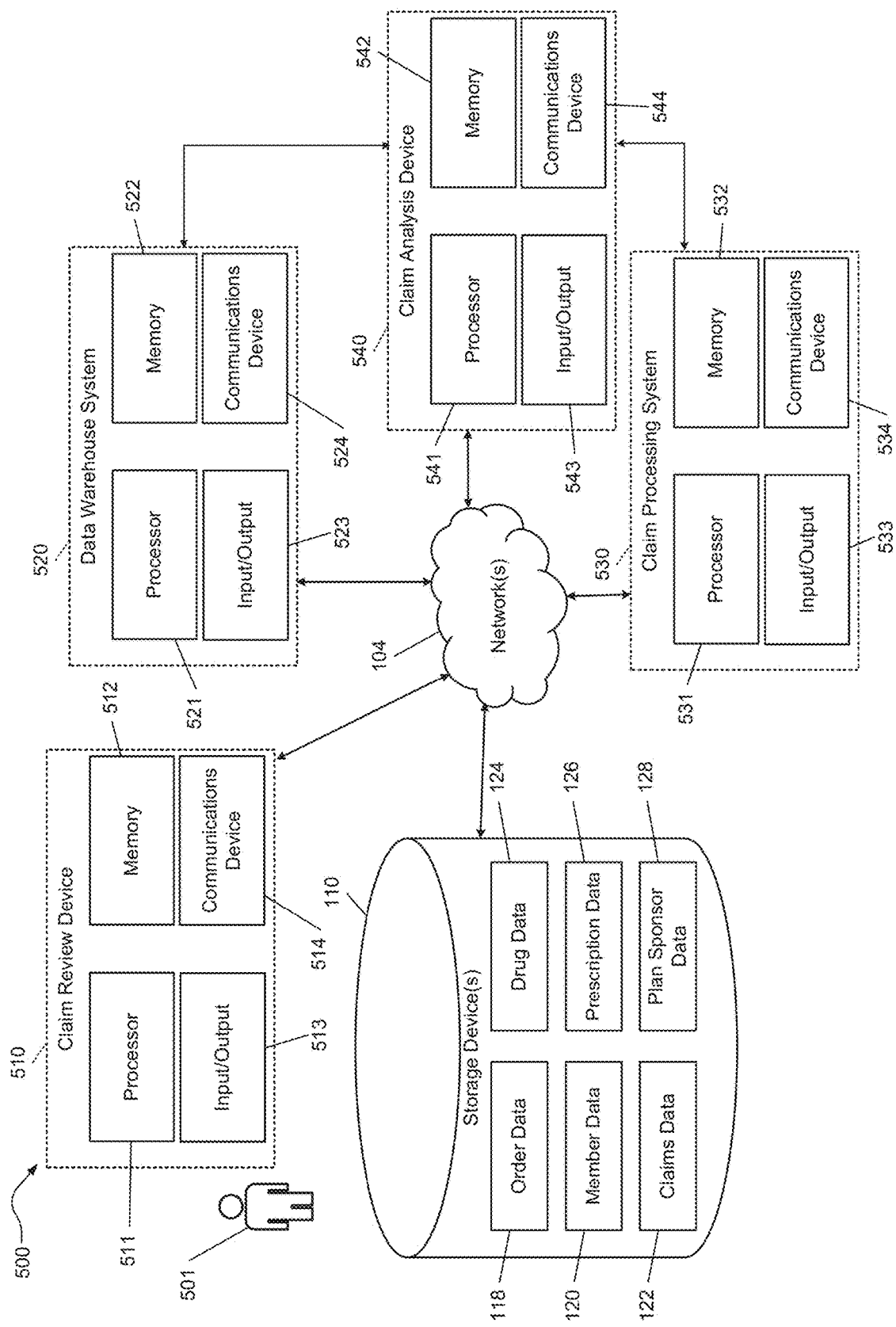
FIG. 5 is a functional block diagram of a machine learning system that may be deployed within the system of FIG. 1 using the computing devices shown in FIG. 4.

FIG. 4 is a functional block diagram of an example computing device 400 that may be used in the machine learning systems described, and may represent the data warehouse system, claim processing system, claim review device, and claim analysis device (all shown in FIG. 5.) Specifically, computing device 400 illustrates an exemplary configuration of a computing device for the systems shown herein, and particularly in FIGS. 1 and 5. Computing device 400 illustrates an exemplary configuration of a computing device operated by a user 401 in accordance with one embodiment of the present invention. Computing device 400 may include, but is not limited to, the data warehouse system, claim processing system, claim review device, and claim analysis device (all shown in FIG. 5.), other user systems, and other server systems. Computing device 400 may also include pharmacy devices 106 including pharmacy fulfillment devices 112, order processing devices 114, and pharmacy management devices 116, storage devices 110, benefit manager devices 102, and user devices 108 (all shown in FIG. 1), mobile computing devices, stationary computing devices, computing peripheral devices, smart phones, wearable computing devices, medical computing devices, and vehicular computing devices. Alternatively, computing device 400 may be any computing device capable of the machine learning methods for predicting whether a prescription or medical claim has an error, particularly in its billing attributes. In some variations, the characteristics of the described components may be more or less advanced, primitive, or non-functional.

In the exemplary embodiment, computing device 400 includes a processor 411 for executing instructions. In some embodiments, executable instructions are stored in a memory area 412. Processor 411 may include one or more processing units, for example, a multi-core configuration. Memory area 412 is any device allowing information such as executable instructions and/or written works to be stored and retrieved. Memory area 412 may include one or more computer readable media.

Computing device 400 also includes at least one input/output component 413 for receiving information from and providing information to user 401. In some examples, input/output component 413 may be of limited functionality or non-functional as in the case of some wearable computing devices. In other examples, input/output component 413 is any component capable of conveying information to or receiving information from user 401. In some embodiments, input/output component 413 includes an output adapter such as a video adapter and/or an audio adapter. Input/output component 413 may alternatively include an output device such as a display device, a liquid crystal display (LCD), organic light emitting diode (OLED) display, or "electronic ink" display, or an audio output device, a speaker or headphones. Input/output component 413 may also include any devices, modules, or structures for receiving input from user 401. Input/output component 413 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 413. Input/output component 413 may further include multiple sub-components for carrying out input and output functions.

Computing device 400 may also include a communications interface 414, which may be communicatively coupleable to a remote device such as a remote computing device, a remote server, or any other suitable system. Communication interface 414 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 414 is configured to allow computing device 400 to interface with any other computing device or network using an appropriate wireless or wired communications protocol such as, without limitation, BLUETOOTH®, Ethernet, or IEE 802.11. Communications interface 414 allows computing device 400 to communicate with any other computing devices with which it is in communication or connection.

FIG. 5 is a functional block diagram of a machine learning system 500 that may be deployed within the system of FIG. 1 using the computing device 400 (shown in FIG. 4.). As suggested in FIG. 5, the machine learning system 500 may be used in system 100 (shown in FIG. 1) and utilizes some of the same elements including storage device 110, order data 118, member data 120, claims data 122, drug data 124, prescription data 126, plan sponsor data 128, and is in connection to network 104 which can provide interconnection between and among the systems shown in FIG. 5 and the systems shown in FIG. 1. As shown in FIG. 5, machine learning system 500 includes storage device 110 and components 118, 120, 122, 124, 126, and 128, claim review device 510, data warehouse system 520, claim processing system 530, and claim analysis device 540. The computer systems 510, 520, 530, and 540 each have an associated processor 511, 521, 531, and 541, an associated memory 512, 522, 532, and 542, an associated input/output 513, 523, 533, and 543, and an associated communications device 514, 524, 534, and 544. Such components function in a manner substantially similar to those described in computing device 400. Computer systems 510, 520, 530, and 540 are in communication with one another and storage device(s) 110 either directly or through network(s) 104. As described above, in some embodiments computer systems 510, 520, 530, and 540 are in communication with other devices such as those described in FIG. 1 via network(s) 104.

As described above and herein, machine learning system 500 is configured to predict errors and validate data in pending claims using the methods described herein. Significantly, data warehouse system 520 is configured to store the historical claims described and provide them to claim analysis device 540. In some examples data warehouse system 520 obtains the historical claims from storage device 110 and, in some examples, from claims data 122. In other examples, data warehouse system 520 is substantially integrated with storage device 110. Similarly, claim processing system 530 is configured to store the pending claims described and provide them to claim analysis device 540. In some examples, claim processing system 530 obtains pending claims from storage device 110, and in some examples, from claims data 122. In other examples, claim processing system 530 is substantially integrated with storage device 110. As described, claim analysis device 540 performs the analyses described and, as applicable, provides output to other systems including claim review device 510. Claim review device 510 represents a user terminal that allows an individual user to review claim records and be alerted regarding predicted errors in claims, notified of corrections or modifications of claims based on predicted errors, or notified of suggestions for corrections to predicted errors.

Notably, although machine learning system 500 illustrates systems 510, 520, 530, and 540 as distinct, in some examples they may be integrated with one another. In at least some embodiments, systems 520, 530, and 540 are integrated into a single system capable of performing the processes described herein.

Figure 6:
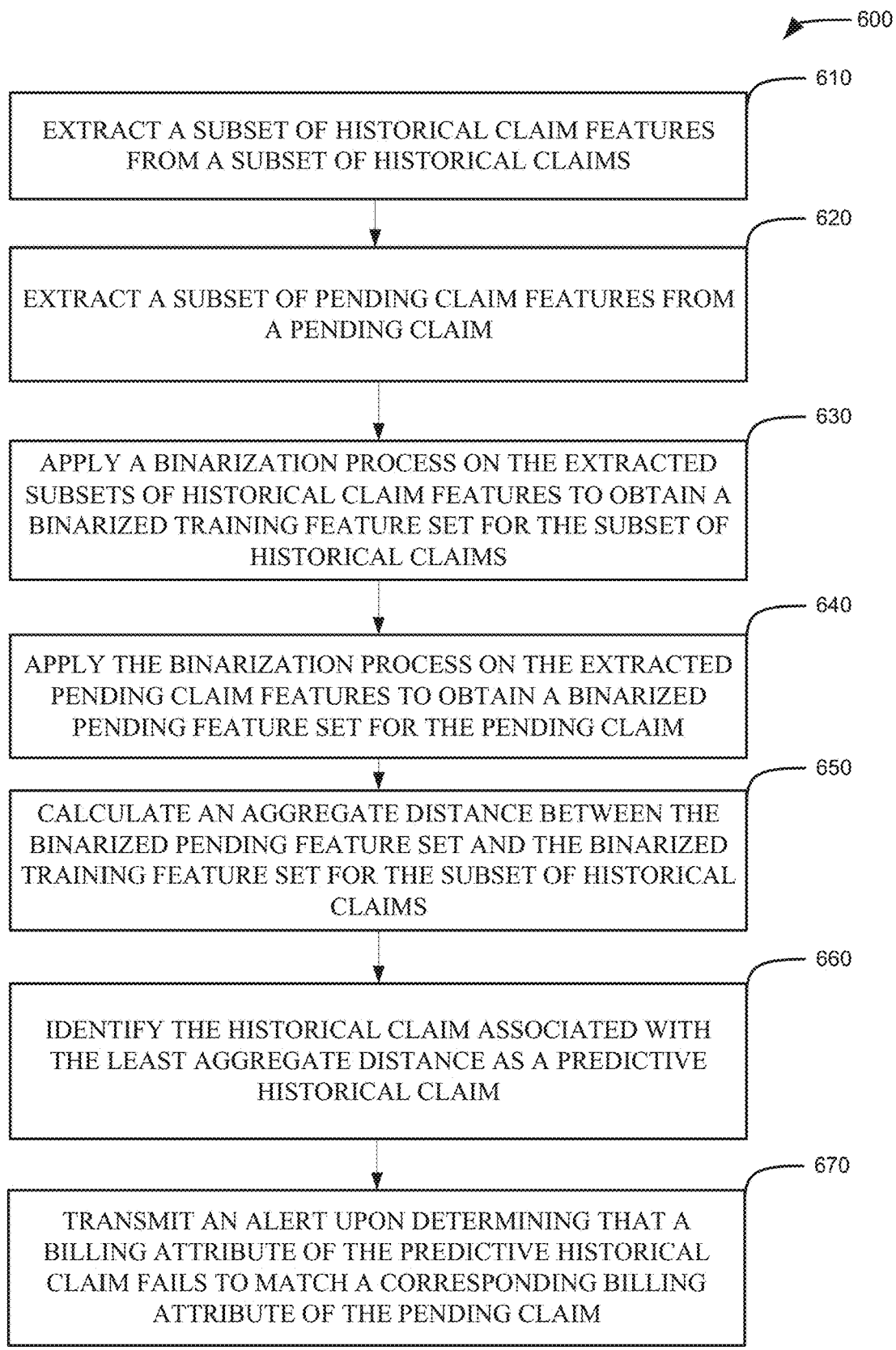
FIG. 6 is a flow diagram representing the error prediction process from the perspective of the claim analysis device shown in FIG. 5.

FIG. 6 is a flow diagram 600 representing the error prediction and analysis process described from the perspective of the claim analysis device 540 (shown in FIG. 5.) Flow diagram 600 depicts the exemplary steps that are executed by claim analysis device 540 in the context of machine learning system 500 (shown in FIG. 5).

In the example embodiment, claim analysis device 540 extracts 610 a subset of historical claim features from each of a subset of historical claims received from the data warehouse system. Each of the subset of historical claims has a corresponding historical claim status indicating that the claim has been successfully processed. Claim analysis device 540 also extracts 620 a subset of pending claim features from a pending claim received from the claim processing system. Claim analysis device 540 additionally applies 630 a binarization process on the extracted subsets of historical claim features to obtain a binarized training feature set for each of the subset of historical claims. Claim analysis device 540 also applies 640 the binarization process on the extracted pending claim features to obtain a binarized pending feature set for the pending claim. Claim analysis device 540 further calculates 650 an aggregate distance between the binarized pending feature set and the binarized training feature set for each of the subset of historical claims. Claim analysis device 540 also identifies 660 the historical claim associated with the least aggregate distance as a predictive historical claim and transmits 670 an alert upon determining that a billing attribute of the predictive historical claim fails to match a corresponding billing attribute of the pending claim.

Figure 7:
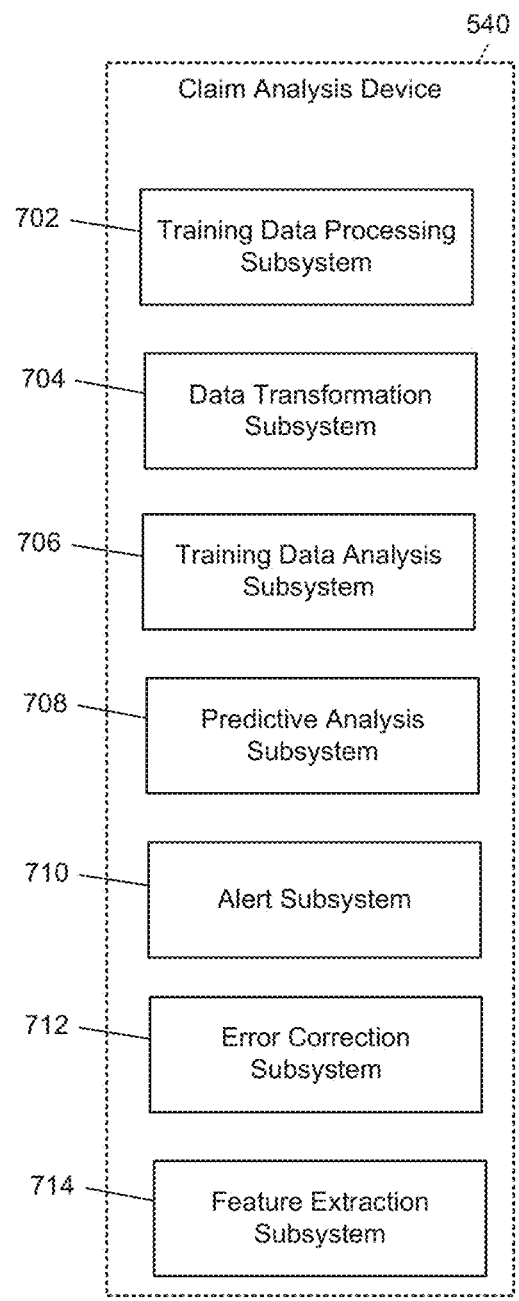
FIG. 7 is a diagram of elements of one or more example computing devices that may be used in the system shown in FIGS. 1 and 5.

FIG. 7 is a diagram of elements of one or more example computing devices that may be used in the system shown in FIGS. 1 and 5. Specifically, FIG. 7 describes subsystems available to claim analysis device 540 capable of providing the functionality described herein. Claim analysis device 540 includes a training data processing subsystem 702 configured to process historical claims to be used in machine learning models to predict errors in pending claims. Claim analysis device 540 also includes a data transformation subsystem 704 that is configured to perform preliminary processing on the features of claims data and, for example, convert such data to a binary format and any other necessarily data formats to provide the functions herein. Claim analysis device 540 also includes a training data analysis subsystem 706 that is configured to analyze the training data and perform computations including, for example, Hamming distance calculations and aggregations, along with any weightings of the component distances thereof. Claim analysis device 540 further includes a predictive analysis subsystem 708 configured to identify the nearest neighbor historical claim, relative to a pending claim, as a predictive historical claim and identify an expected billing attribute for the pending claim based on the billing attribute of the predictive historical claim. Claim analysis device 540 additionally includes an alert subsystem 710 that transmits an alert to an external system such as a claim review device 510 (shown in FIG. 5) to inform a user 501 (shown in FIG. 5) that a particular pending claim is either a) predicted to have an error, b) validated as not predicted to have an error, c) recommended for a modification to a billing attribute because of a predicted error, or d) has had a billing attribute modified because of a predicted error. Claim analysis device 540 further has an error correction subsystem 712 that is capable of adjusting a particular pending claim (or pending claims) after determining that an error is predicted in the billing attribute. The error correction subsystem 712 is configured to adjust such pending claims to have a billing attribute that is expected based on the machine learning processes described herein. Claim analysis device 540 also has a feature extraction subsystem 714 that is configured to define and manage features for extraction (including managing a list of features for extraction) and perform such extraction from pending claims and historical claims.

Figure 8:
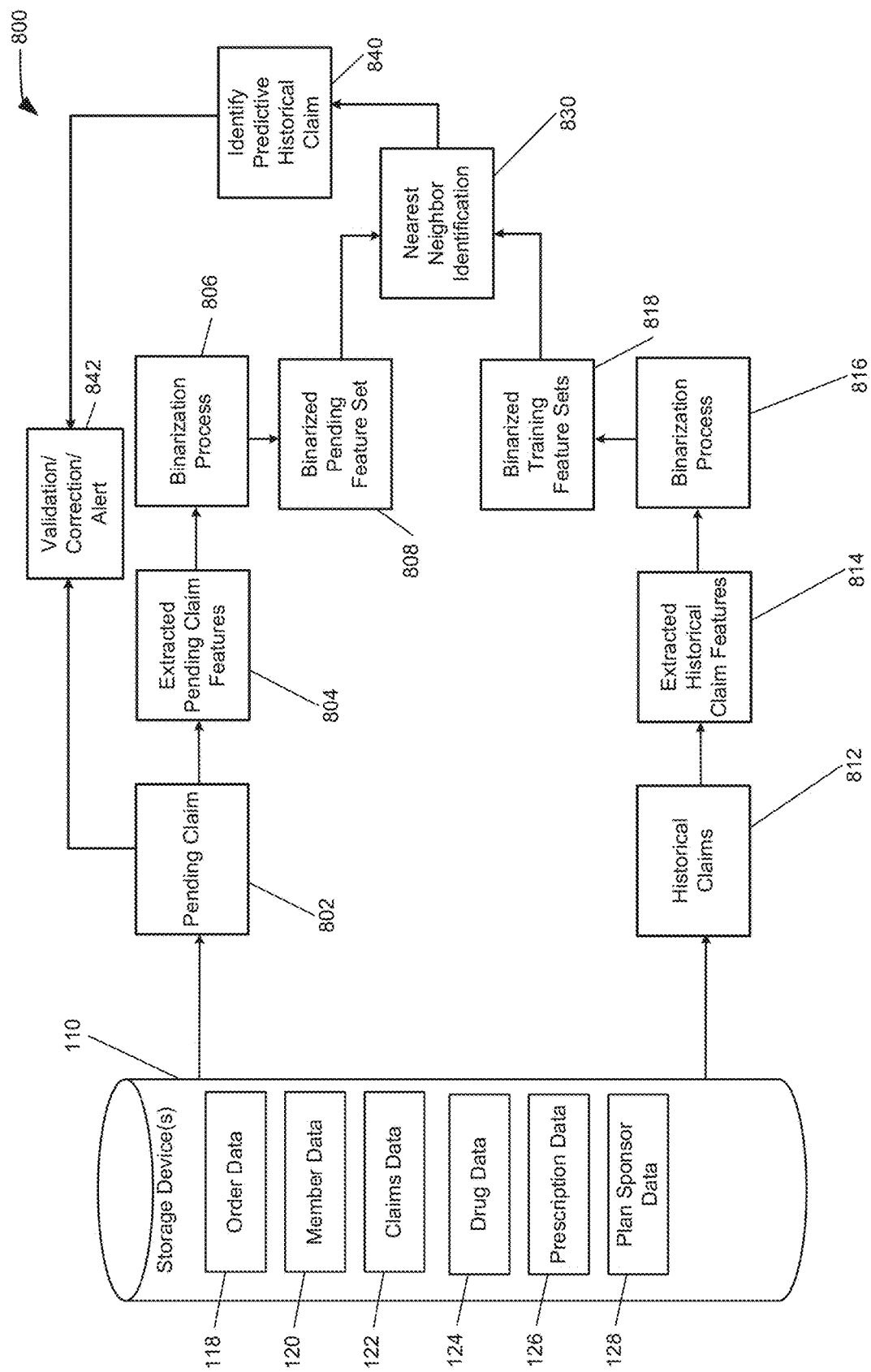
FIG. 8 is a diagram illustrating the data processing workflow in the machine learning system of FIG. 5.

FIG. 8 is a diagram illustrating the data processing workflow 800 in the machine learning system of FIG. 5. Specifically, workflow 800 illustrates the process of obtaining, retrieving, transforming, and analyzing the claim data of prescription (or medical) claims in order to predict errors in attributes such as billing attributes. (The approach described herein can be effective in predicting errors in attributes in other features and values.) As described, process 800 entails machine learning system 500 (and, more specifically, data warehouse system 520) retrieving a pending claim 802 (or pending claims, if in parallel) from storage device 110. Typically pending claim 802 is retrieved from claims data 122. As described, pending claim 802 may be identified in any suitable manner including the relative age of claims (e.g., retrieving the newest or oldest available claim that has not been analyzed and validated or predicted to have an error), flagging by a user or a system, random selection, or particular attributes of the claim (e.g., the geographic location of the claim). Data warehouse system 520 provides pending claim 802 to claim analysis device 540 which extracts the pending claim features 804 and applies a binarization process 806 to obtain a binarized pending feature set 808 to analyze for nearest neighbor identification 830. Process 800 also entails machine learning system 500 (and, more specifically, claim processing system 530) utilizing a bulk data processor (or any other suitable method) to obtain a subset of historical claims 812 from storage device 110. Typically the subset of historical claims 812 is obtained from claims data 122. As described above and herein, the subset is typically a group of recent claims (e.g., claims filed within a recent period of the past hours, days, or week) that were successfully processed for payment with representative sampling for the relevant predictive attribute (e.g., billing attributes). Claim processing system 530 provides the subset of historical claims 812 to claim analysis device 540 which extracts the historical claim features 814 and applies a binarization process 816 to obtain a binarized training feature set 818 for analysis by nearest neighbor identification 830. Claim analysis device 540 performs the described methods of calculating distances between each of the binarized training features sets 818 and the binarized pending features set 808 to identify a predictive historical claim 840. Based on the identified predictive historical claim 840, claim analysis device 540 performs necessary validations, corrections, and alerts 842 by comparing the identified predictive historical claim 840 to the pending claim 802. As noted above, in some embodiments, data warehouse system 520, claim processing system 530, and claim analysis device 540 are integrated into a single system.

FIG. 9 is a flow diagram representing an exemplary process 900 performed by the machine learning system of FIG. 5 to predict errors in data processing systems. Like FIG. 8, FIG. 9 is an exemplary illustration of a workflow that may be performed using the systems and methods described. In other examples, these workflows may vary. In process 900, a user such as user 501 may access a device such as claim review device 510 and request a predictive analysis 912. (In many examples, this process is automated and does not require a user to initiate request 912.) Request 912 is received by application interface 901 which relays request 912 as a request to the application program interface ("API") of a communication framework 902 used to manage the intercommunication between machine learning system 500 (shown in FIG. 5), including its component systems, and other systems such as claim review device 510. Communication framework 902 processes the API request 914 and converts it into a request for historical claims 916 from a machine learning model 903 to use in training. In some examples, machine learning model is located within machine learning system and/or claim analysis device 540. Machine learning model 903 processes request 916 and converts it into a request for training data 918 to send to data warehouse system 520. Data warehouse system 520 provides training data 920 in response to machine learning model 903 which receives pending claims 922 from communication framework 902. Pending claims 922 are available from communication framework 902 based on the initial request 912 made by claim review device 510 to review a particular pending claim or claims. Machine learning model 903 processes the pending claims 922 and identifies a nearest neighbor based on training data 920 to identify a nearest neighbor as a predictive historical claim 924. Communication framework 902 initiates a validation process 926 to determine whether the relevant attribute (such as the billing attribute) of the pending claim corresponds to the corresponding attribute of the predictive historical claim 924. Application interface 901 may initiate any necessary resolution 928 including sending an alert to claim review device 510 advising of an error or a validation, recommending an edit to be made to an attribute based on the predicted error, or automatically editing an attribute based on a predicted error.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A machine learning system for use in dispensing one or more prescription drugs, the machine learning system comprising:
   a data warehouse system comprising a data warehouse processor and a data warehouse memory, the data warehouse memory including historical claims, wherein the historical claims include a set of historical claim features and a historical claim status;
   a claim processing system comprising a system processor and a system memory, the system memory including pending claims, wherein the pending claims include a set of pending claim features;
   a pharmacy fulfillment device configured to dispense a prescription drug; and
   a claim analysis device in communication with the data warehouse system, the claim processing system, and the pharmacy fulfillment device, the claim analysis device comprising a processor and a memory, wherein the processor is configured to:
   extract subsets of historical claim features from a subset of historical claims received from the data warehouse system, wherein each of the subset of historical claims has a corresponding historical claim status indicating that the claim has been successfully processed;
   extract a subset of pending claim features from a pending claim received from the claim processing system;
   apply a binarization process on the extracted subsets of historical claim features to obtain a binarized training feature set for the subset of historical claims;
   apply the binarization process on the extracted subset of pending claim features to obtain a binarized pending feature set for the pending claim;
   calculate an aggregate distance between the binarized pending feature set and the binarized training feature set for the subset of historical claims;
   identify, from the subset of historical claims, a historical claim associated with the least aggregate distance as a predictive historical claim;
   determine that a billing attribute of the predictive historical claim matches a corresponding billing attribute of the pending claim, validate the pending claim and transmit, to the pharmacy fulfillment device, an instruction for dispensing the prescription drug in accordance with the pending claim,
wherein the pharmacy fulfillment device is further configured to dispense the prescription drug based on the instruction from the claim analysis device.

2. The machine learning system of claim 1, wherein the processor is further configured to:
calculate a distance between the features of the binarized pending feature set and the corresponding features of the binarized training feature set for the subset of historical claims; and
process the distance determined for the features of the binarized pending feature set and the corresponding features of the binarized training feature set for the subset of historical claims, to determine the aggregate distance between the binarized pending feature set and the binarized training feature set for the subset of historical claims.

3. The machine learning system of claim 1, wherein the processor is further configured to:
calculate the aggregate distance based on a calculated Hamming distance between the binarized pending feature set and the binarized training feature set for the subset of historical claims.

4. The machine learning system of claim 1, wherein the processor is further configured to:
define the binarization process as encoding the features of a feature set in a corresponding binary format.

5. The machine learning system of claim 1, wherein the processor is further configured to:
identify a list of features for feature extraction based on a feature analysis profile;
extract the subsets of historical claim features matching the list of features; and
extract the subset of pending claim features matching the list of features.

6. The machine learning system of claim 5, wherein the processor is further configured to:
identify the list of features for feature extraction including at least one of a processor identification number, a processor control number, and a therapy type.

7. The machine learning system of claim 1, wherein the processor is further configured to:
transmit a request to the data warehouse system for the subset of historical claims with corresponding historical claim statuses indicating that the claims have been successfully resolved; and
receive the subset of historical claims from the data warehouse system.

8. A method for use in dispensing one or more prescription drugs, said method performed by a claim analysis device and a pharmacy fulfillment device in communication with a data warehouse system and a claim processing system, the data warehouse system including historical claims including a set of historical claim features and a historical claim status, the claim processing system including pending claims including a set of pending claim features, the pharmacy fulfillment device configured to dispense a prescription drug, the claim analysis device including a processor and a memory, said method comprising:
extracting, by the claim analysis device, subsets of historical claim features from a subset of historical claims received from the data warehouse system, wherein each of the subset of historical claims has a corresponding historical claim status indicating that the claim has been successfully processed;
extracting, by the claim analysis device, a subset of pending claim features from a pending claim received from the claim processing system;
applying, by the claim analysis device, a binarization process on the extracted subsets of historical claim features to obtain a binarized training feature set for the subset of historical claims;
applying, by the claim analysis device, the binarization process on the extracted subset of pending claim features to obtain a binarized pending feature set for the pending claim;
calculating, by the claim analysis device, an aggregate distance between the binarized pending feature set and the binarized training feature set for the subset of historical claims;
identifying, by the claim analysis device, from the subset of historical claims, a historical claim associated with the least aggregate distance as a predictive historical claim;
determining, by the claim analysis device, that a billing attribute of the predictive historical claim matches a corresponding billing attribute of the pending claim;
validating, by the claim analysis device, the pending claim and transmitting, to the pharmacy fulfillment device, an instruction for dispensing the prescription drug in accordance with the pending claim; and
dispensing, by the pharmacy fulfillment device, the prescription drug based on the instruction from the claim analysis device.

9. The method of claim 8, further comprising:
calculating, by the claim analysis device, a distance between the features of the binarized pending feature set and the corresponding features of the binarized training feature set for the subset of historical claims; and
processing, by the claim analysis device, the distance determined for the features of the binarized pending feature set and the corresponding features of the binarized training feature set for the subset of historical claims, to determine the aggregate distance between the binarized pending feature set and the binarized training feature set for the subset of historical claims.

10. The method of claim 8, further comprising:
calculating, by the claim analysis device, the aggregate distance based on a calculated Hamming distance between the binarized pending feature set and the binarized training feature set for the subset of historical claims.

11. The method of claim 8, further comprising:
defining, by the claim analysis device, the binarization process as encoding the features of a feature set in a corresponding binary format.

12. The method of claim 8, further comprising:
identifying, by the claim analysis device, a list of features for feature extraction based on a feature analysis profile;
extracting, by the claim analysis device, the subsets of historical claim features matching the list of features; and
extracting, by the claim analysis device, the subset of pending claim features matching the list of features.

13. The method of claim 12, further comprising:
identifying, by the claim analysis device, the list of features for feature extraction including at least one of a processor identification number, a processor control number, and a therapy type.

14. The method of claim 8, further comprising:
transmitting, by the claim analysis device, a request to the data warehouse system for the subset of historical claims with corresponding historical claim statuses indicating that the claims have been successfully resolved; and
receiving, by the claim analysis device, the subset of historical claims from the data warehouse system.

15. A system comprising a first non-transitory computer readable storage medium of a claim analysis device and a second non-transitory computer readable storage medium of a pharmacy fulfillment device,
the first non-transitory computer readable storage medium having stored thereon a first set of instructions for processing instructions of a software program that when executed by the claim analysis device, causes the claim analysis device to:
extract subsets of historical claim features from a subset of historical claims received from a data warehouse system, wherein each of the subset of historical claims has a corresponding historical claim status indicating that the claim has been successfully processed;
extract a subset of pending claim features from a pending claim received from a claim processing system;
apply a binarization process on the extracted subsets of historical claim features to obtain a binarized training feature set for the subset of historical claims;
apply the binarization process on the extracted subset of pending claim features to obtain a binarized pending feature set for the pending claim;
calculate an aggregate distance between the binarized pending feature set and the binarized training feature set for the subset of historical claims;
identify, from the subset of historical claims, a historical claim associated with the least aggregate distance as a predictive historical claim;
determine that a billing attribute of the predictive historical claim matches a corresponding billing attribute of the pending claim;
validate the pending claim and transmit an instruction to the pharmacy fulfillment device for dispensing the prescription drug in accordance with the pending claim; and
the second non-transitory computer readable storage medium of the pharmacy fulfillment device having stored thereon a second set of instructions that, when executed by the pharmacy fulfillment device, cause the pharmacy fulfillment device to:
dispense the prescription drug based on the instruction from the claim analysis device.

16. The system of claim 15, wherein the software program when executed by the claim analysis device, causes the claim analysis device to:
calculate a distance between the features of the binarized pending feature set and the corresponding features of the binarized training feature set for the subset of historical claims; and
process the distance determined for the features of the binarized pending feature set and the corresponding features of the binarized training feature set for the subset of historical claims, to determine the aggregate distance between the binarized pending feature set and the binarized training feature set for the subset of historical claims.

17. The system of claim 15, wherein the software program when executed by the claim analysis device, causes the claim analysis device to:
calculate the aggregate distance based on a calculated Hamming distance between the binarized pending feature set and the binarized training feature set for the subset of historical claims.

18. The system of claim 15, wherein the software program when executed by the claim analysis device, causes the claim analysis device to:
define the binarization process as encoding the features of a feature set in a corresponding binary format.

19. The system of claim 15, wherein the software program when executed by the claim analysis device, causes the claim analysis device to:
identify a list of features for feature extraction based on a feature analysis profile;
extract the subsets of historical claim features matching the list of features; and
extract the subset of pending claim features matching the list of features.

20. The system of claim 15, wherein the software program when executed by the claim analysis device, causes the claim analysis device to:
identify the list of features for feature extraction including at least one of a processor identification number, a processor control number, and a therapy type.

* * * * *